US010849732B2

(12) United States Patent
Barone

(10) Patent No.: US 10,849,732 B2
(45) Date of Patent: Dec. 1, 2020

(54) PROSTHESIS FOR TREATING ABDOMINAL AORTIC ANEURYSM AND METHOD

(71) Applicant: Hector Daniel Barone, Buenos Aires (AR)

(72) Inventor: Hector Daniel Barone, Buenos Aires (AR)

(*) Notice: Subject to any disclaimer, the term of this patent is extended or adjusted under 35 U.S.C. 154(b) by 41 days.

(21) Appl. No.: 16/085,303

(22) PCT Filed: Apr. 25, 2017

(86) PCT No.: PCT/EP2017/059770
§ 371 (c)(1),
(2) Date: Sep. 14, 2018

(87) PCT Pub. No.: WO2017/186706
PCT Pub. Date: Nov. 2, 2017

(65) Prior Publication Data
US 2019/0083227 A1    Mar. 21, 2019

(30) Foreign Application Priority Data
Apr. 27, 2016 (AR) .......................... P20160101195

(51) Int. Cl.
*A61F 2/07* (2013.01)
*A61F 2/06* (2013.01)
(Continued)

(52) U.S. Cl.
CPC ................ *A61F 2/07* (2013.01); *A61F 2/90* (2013.01); *A61F 2/958* (2013.01);
(Continued)

(58) Field of Classification Search
CPC .... A61F 2/07; A61F 2/90; A61F 2/958; A61F 2002/065; A61F 2002/067;
(Continued)

(56) References Cited

U.S. PATENT DOCUMENTS 4,562,596 A    1/1986 Kornberg
4,922,905 A    5/1990 Strecker
(Continued)

FOREIGN PATENT DOCUMENTS

EP    2 074 960 A1    7/2009
WO    83/03752 A1    11/1983
(Continued)

OTHER PUBLICATIONS

International Search Report dated Jun. 28, 2017, dated Jul. 5, 2017.

*Primary Examiner* — Brian A Dukert
*Assistant Examiner* — Amanda M Barkan
(74) *Attorney, Agent, or Firm* — Norris McLaughlin, P.A.

(57) ABSTRACT

An aortic prosthesis for the treatment of abdominal aortic aneurysms, wherein the prosthesis is implanted intraluminally and comprises a main body having a generally cylindrical shape with an upper portion intended to be secured firmly above the renal arteries through an anchoring means, a lower portion freely moving at a position within the aneurysm and above the iliac arteries, and an intermediate portion arranged between the upper and lower portions, and the main body comprising a flexible fabric of woven material having a very loose weave in the upper portion so as to allow fluid communication between the interior of the prosthesis and the renal arteries, an intermediate weave in the intermediate portion and a tight weave in the lower portion of the main body.

16 Claims, 7 Drawing Sheets

(51) Int. Cl.
*A61F 2/90* (2013.01)
*A61F 2/958* (2013.01)

(52) U.S. Cl.
CPC ... *A61F 2002/065* (2013.01); *A61F 2002/075* (2013.01); *A61F 2250/0015* (2013.01)

(58) Field of Classification Search
CPC .......... A61F 2002/068; A61F 2002/077; A61F 2002/823; A61F 2002/852
See application file for complete search history.

(56) References Cited

U.S. PATENT DOCUMENTS

| | | | |
|---|---|---|---|
| 5,609,627 A | 3/1997 | Goicoechea et al. | |
| 5,628,788 A | 5/1997 | Pinchuk | |
| 5,632,772 A | 5/1997 | Alcime et al. | |
| 5,639,278 A | 6/1997 | Dereume et al. | |
| 6,162,246 A * | 12/2000 | Barone | A61F 2/07 623/1.35 |
| 6,344,056 B1 * | 2/2002 | Dehdashtian | A61F 2/07 623/1.35 |
| 6,554,855 B1 * | 4/2003 | Dong | A61F 2/07 623/1.13 |
| 8,353,943 B2 * | 1/2013 | Kuppurathanam | A61F 2/07 623/1.1 |
| 8,728,151 B2 | 5/2014 | Goldmann et al. | |
| 8,900,287 B2 * | 12/2014 | Amplatz | A61F 2/07 623/1.13 |
| 2009/0171450 A1 | 7/2009 | Goldmann et al. | |
| 2010/0094390 A1 | 4/2010 | Goldmann et al. | |
| 2016/0157990 A1 * | 6/2016 | Shalev | A61F 2/07 623/1.12 |

FOREIGN PATENT DOCUMENTS

| | | |
|---|---|---|
| WO | 90/15582 A1 | 12/1990 |
| WO | 02/35989 A2 | 5/2002 |
| WO | 2005/081936 A1 | 9/2005 |
| WO | 2008/083767 A1 | 7/2008 |

* cited by examiner

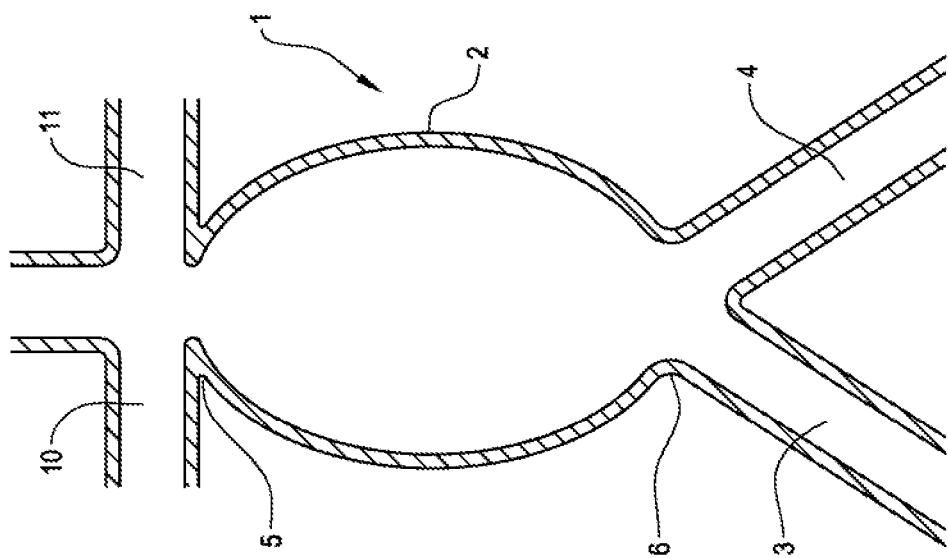
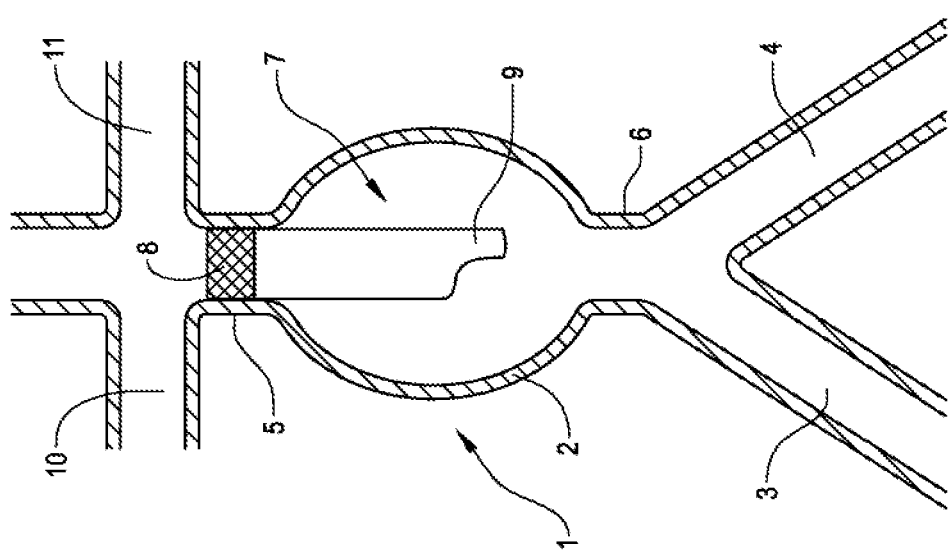

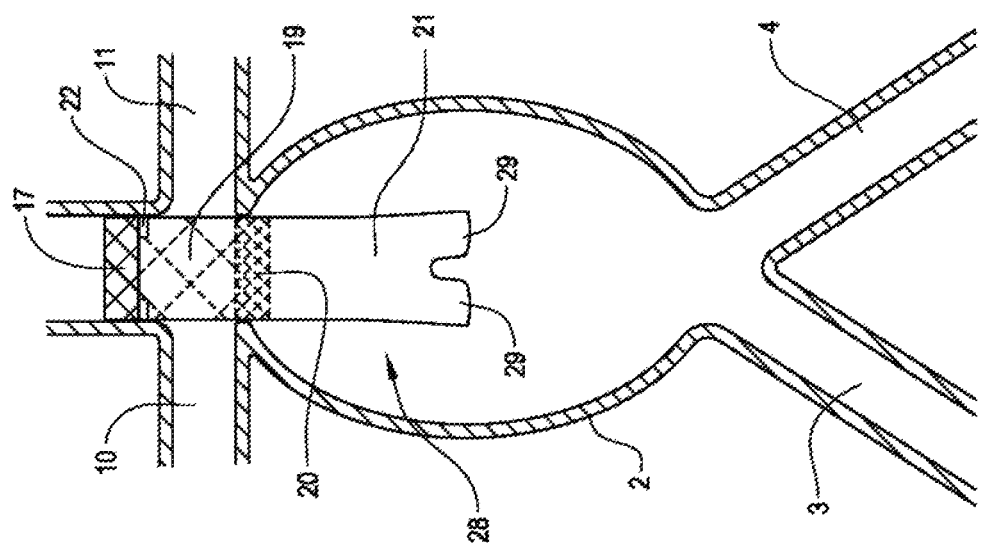
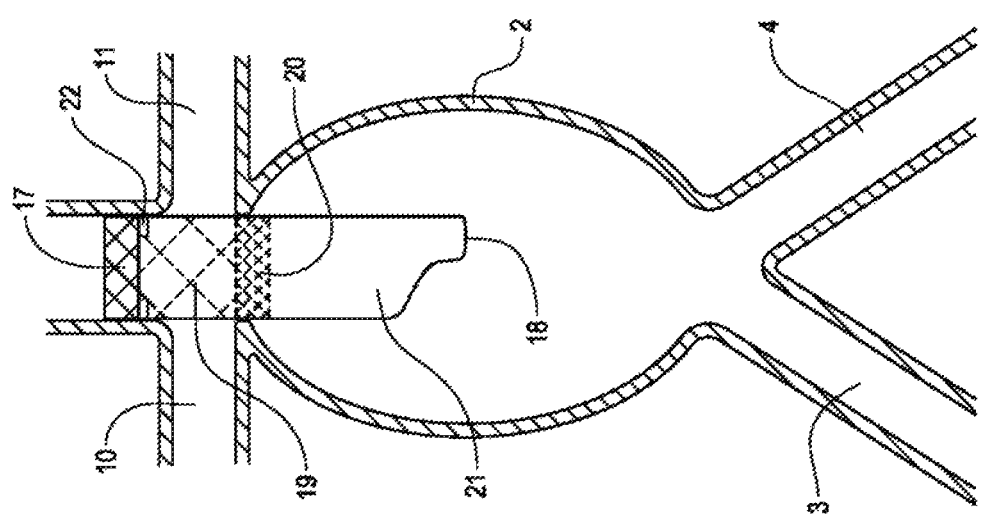

PROSTHESIS FOR TREATING ABDOMINAL AORTIC ANEURYSM AND METHOD

BACKGROUND OF THE INVENTION

This application is a 371 application of PCT/EP2017/059770 filed Apr. 25, 2017, which claims foreign priority benefit under 35 U.S.C. § 119 of Argentina Patent Application P 20160101195 filed Apr. 27, 2016, the disclosures of which are incorporated herein by reference.

1. Field of the Invention

The present invention relates to an aortic prosthesis for the treatment of abdominal aneurysms and in particular relates to a prosthesis for the intraluminal repair of aortic aneurysms by positioning the prosthesis above and in the area within the aneurysm, the prosthesis comprising a design and structure that facilitates and ensures a safe and effective assembly or implantation thereof even when the aneurysm affects the portion of an upper proximal aortic neck where the prosthesis is usually anchored, this differentiates the novel prosthesis from conventional monoiliac and bifurcated prostheses, which can not be efficiently implanted when the aortic neck portion is not healthy.

2. Description of the Prior Art

The aorta is the main trunk of the arterial system, starting from the heart and extending down through the thorax and through the abdomen and then is divided into two iliac arteries. An abdominal aortic aneurysm is an abnormal dilatation of the aortic wall in the area of the aorta that passes through the abdomen. The aneurysm should be treated to prevent its rupture. If the aneurysm is not treated, the sac will eventually rupture resulting in fatal hemorrhages in a very short time. This usually leads to the death of the individual suffering from the aneurysm, and today the mortality resulting from this abnormality is so high that new and improved techniques are constantly being sought to solve this pathology. Although open surgery has been the way of treatment for many years, surgical repair of the aortic wall is associated with a high risk, particularly in elderly patients.

Search for alternative techniques that do not involve surgery has been a concern of professionals in the art. U.S. Pat. No. 4,562,596 to Elliot Kornberg et al. discloses a bifurcated aortic prosthesis which is specifically designed for intraluminal insertion and comprises a hollow, generally cylindrical sleeve and sleeve made of one piece, having an upper end intended to be attached to a proximal upper neck of the aorta, upstream the aneurysm, and a minor axis and a major axis defining two lower legs or extensions which are intended to be inserted within a respective iliac artery below the aneurysm, so as to form a continuous fluid path within the aorta, excluding the damaged aortic wall, i.e. the aneurysm, from the blood flow.

U.S. Pat. No. 4,922,905 relates to a catheter and discloses a tubular stent device having a wall structure comprising a tube-like knitted loose woven fabric made of loosely interwoven loops of metal filament material, said tube-like fabric being deformed radially inward with respect to its knitted fabric conformation and is capable of being progressively and permanently deformed with radial expansion by means of the catheter in order to fix the stent into a blood vessel to be repaired.

Patent WO 83/03752 to Wallsten, Hans Ivar, discloses a prosthesis comprising a one-piece expandable tubular body to be inserted into a vascular conduit.

Patent WO 90/15582 to Trout, Hugh discloses an aortic graft or prosthesis comprising a substantially cylindrical prosthesis material with fixing means which comprise a plurality of sets of protrusions and hooks to provide a secured fixation of the aortic prosthesis against the aortic wall.

While many graft or prostheses structures have been developed, all of them have been developed in connection with the improvement of their materials, new fixation means, expandable fixing means "stents" and/or new devices for arranging and installing the graft within the blood vessel. However, the location and proper arrangement of the prosthesis within the blood conduit, particularly a prosthesis designed for the repair of aortic aneurysms, is not an easy task insofar as the aorta is the largest blood conduit with a shape requiring that special consideration be taken not only with regard to the dilated wall but also to those portions of the wall which are in good condition and available to securely fix the prosthesis in the aorta.

An obstacle encountered during the choice of prosthesis for a given patient is that the length of the aorta is not the same for all patients and, even for the same patient, the aorta has an internal diameter in the aortic upper neck or proximal neck and the iliac arteries have a different smaller diameter. In addition, the relationship between the aortic diameter and the iliac artery diameter is not always the same, and therefore, today it is necessary to have a large number of grafts or prostheses that combine in a large number of upper diameters, for the aortic neck, and lower diameters, for the iliac arteries.

The problem of the different sizes and shapes of the aortas is also an important issue when the upper end of the graft is placed in the correct place in the proximal aortic neck to obtain a secured fixation of the prosthesis in the neck and to seal the graft against the neck of the aorta so as to prevent blood from flowing through the graft and escaping out of it and entering the excluded aneurysm. That is, the blood flow must circulate only in a restricted manner within the graft or prosthesis without there being any loss occurring at the attachment site. The prosthesis includes, at each end thereof, anchoring means, referred to as "stents", wherein each stent is firmly attached to each end of the prosthesis and frequently a portion of each stent extends beyond the associated end, and said extended portion is designed to anchor against the iliac or aortic walls. Therefore, if the aneurysm neck is not long enough, it may happen that the stent remains firmly attached to the aorta without the end of the prosthesis material being properly arranged and sealed against the wall of the aortic neck. In this situation, the prosthesis will be firmly held against the aortic wall but the prosthesis material will not be sealed against the aortic neck at the fixation site.

Another issue is that the diameter of the aortic neck should be carefully considered when selecting the prosthesis. If the prosthesis has insufficient diameter to fit the diameter of the aortic neck, there will be a loss of blood through a space or span that will be formed between the prosthesis and the aortic wall. If the diameter of the prosthesis is excessive, the upper edge of the prosthesis will fold, forming small spaces between the prosthesis and the aortic wall, thereby causing the aforementioned problems of blood loss. This problem is solved in part by prostheses made of elastic or resilient fabric with fasteners or stents made of a constructive material that can be deformed by means of an expandable balloon and can maintain a final deformed diameter. The use of resilient fixing means, or also called "self-expanding" fixing means, has drawbacks because the excessive diameter thereof causes the aortic wall to be permanently subjected to an expanding force which affects the integrity thereof.

U.S. Pat. No. 5,609,627 to Goicoechea et al. discloses a bifurcated prosthesis comprising a wire skeleton constructed in various parts made of nitinol wire and lined by a layer of prosthesis fabric. The nitinol wire, although flexible in a cold state, behaves like a steel wire at the temperature inside the patient's body. As also described in this patent, Goicoechea also proposes a method for installing this prosthesis, which consists of arranging a first bifurcated part and then entering this part through the lower ends thereof to introduce additional prosthetic legs and connect them to lower openings in the bifurcated portion.

U.S. Pat. No. 5,628,788 to Pinchuk et al.; U.S. Pat. No. 5,632,772 under the name of Alcime et al. and U.S. Pat. No. 5,639,278 under the name of Dereume et al., disclose endoluminal prostheses which are both expandable and supportive and comprise a supporting fixing means or stent made of resilient wire elements and a cover or lining made of a porous material arranged on or inside the supporting wire structure.

Briefly, when a prosthesis composed of a support and a lining is intended to be adapted within a tortuous aorta and, because of its rigidity, the prosthesis does not properly seat and seal against the aortic neck since the upper end of the prosthesis is forced through the tortuous aortic lumen and the prosthesis tends to adopt a straight configuration without copying the curved or tortuous aortic lumen. It is very common for this type of prosthesis to remain fixed in the aortic neck in an inclined configuration because when all guide wires and introducers are removed from the aorta, once the prosthesis has been deployed therein, the aorta tends to return to its original tortuous configuration. Since the prosthesis can not adapt to this configuration, the forces exerted by the aorta to recover its initial position are transferred directly to the prosthesis causing it to alter its initial connection in the aortic neck. Same alterations occur in the legs of the prosthesis that are connected to the main prosthesis portion and the iliac arteries.

In addition to the above, it is also well known that the aortic neck is not always straight and it may be inclined with respect to the vertical axis of the patients body. Under these circumstances a prosthesis made of wires like the one described above can not be adapted to this inclination. A similar problem is encountered when the inner wall of the aortic neck is not entirely circular but has calciferous formations that make the neck inner wall irregular. This irregular perimeter may not be "copied" by a self-expanding prosthesis, which leaves portions of the aortic wall unsealed and results in loss of blood flow. If, in order to solve any of these problems concerning irregularities in the aortic neck, the prosthesis is placed in a higher position, upwards, beyond the renal arteries, the flow through these arteries is blocked by the prosthesis that is composed of a dense mesh or a membrane of very low porosity. Of course, if the renal arteries are occluded by the wrongly placed prosthesis, patients life is threatened by lack of blood to kidneys resulting in inevitable death within hours.

Although the above drawbacks have been satisfactorily solved by the U.S. Pat. No. 6,162,246 of the same owner as this application, a drawback has been observed regarding the condition of the aneurysm and its effect on the area of the superior proximal aortic neck. If the aneurysm extends and dilates in such a way that it does not have a superior aortic neck or the neck is very short, conventional prostheses or grafts used today could not be deployed due to their structural configuration. Conventional prostheses consist of a tubular impermeable fabric throughout their length to isolate the aneurysm, and the fabric has therein, and at least at its ends, anchoring means, "stents", which upon expansion fix and seal the upper end of the fabric "tube" against the wall of the aneurysm neck. As said above, if this neck, which is immediately below the renal arteries, is not healthy, or is very short, the doctor tends to place the tube higher, looking for a healthier and firmer wall, and in this placement, further up, there is a risk of affecting the ostia of renal arteries by occluding them with the tube.

It would therefore be convenient to have a new aortic prosthesis for the treatment of abdominal aneurysms capable of being easily deployed and not occluding, temporarily or permanently, renal arteries during its installation, even if there is no well defined upper proximal aortic neck, in the area of the abdominal aneurysm, where the upper end of the prosthesis can be fixed.

SUMMARY OF THE INVENTION

It is therefore an object of the present invention to provide an aortic prosthesis which can be deployed in the aorta to treat the abdominal aneurysm even if a healthy and firm upper proximal aortic neck where to anchor the prosthesis is not defined.

It is yet another object of the present invention to provide an aortic prosthesis for use in the repair of abdominal aortic aneurysms by insertion of the prosthesis into the aorta to exclude the aneurysm from the blood circulatory system, the prosthesis comprising a flexible fabric material defined by three different sections, woven without continuity solution, suitable for each area of the aorta.

It is yet another object of the present invention to provide an aortic prosthesis comprising a main body defined by an upper portion which is anchored or secured securely through an anchoring means in a portion of the aorta above the renal arteries without obstructing them.

It is a further object of the present invention to provide an aortic prosthesis comprising a tubular mesh of three weaves differentiated by the density of meshes: a very loose weave, an intermediate weave and a tight weave, the very loose weave being arranged adjacent to the position of the renal arteries and allowing the passage of blood flow to them.

It is yet another object of the present invention to provide an aortic prosthesis comprising a tubular mesh with three sections differentiated by porosity and two renal prostheses complementary to the aortic prosthesis, which ensures blood flow from the aorta to the renal arteries.

It is another object of the present invention to provide an aortic prosthesis deployed via the intraluminal in the aorta.

It is still another object of the present invention to provide a knitted or jersey aortic prosthesis.

It is yet another object of the present invention to provide an aortic prosthesis for the treatment of abdominal aortic aneurysms, wherein the prosthesis comprises a hollow tubular structure intended to be inserted intraluminally into the aorta, wherein the aorta has a portion below which there are two renal arteries, an upper proximal aortic neck and a distal lower aortic portion that forms an iliac bifurcation that is divided into two iliac arteries, wherein the prosthesis comprises a main body having a generally cylindrical shape with an upper portion intended, at least partially, to be secured firmly above the renal arteries through an anchoring means and intended, at least partially, to be freely arranged at the position of the renal arteries, an intermediate portion arranged between the renal arteries and the superior proximal aortic neck, and a lower portion freely moving at a position within the aneurysm and above the iliac arteries, wherein said main body comprises a flexible fabric made of woven material having a very loose weave in said upper portion, an intermediate weave in said intermediate portion and a tight weave in said lower portion of the main body.

It is a further object of the present invention to provide a method for the implantation of an aortic prosthesis in the area of an aorta affected by an aneurysm, wherein the aortic prosthesis comprises a main body having a generally cylindrical shape with an upper portion intended, at least partially, to be firmly secured above the renal arteries through an anchoring means and intended, at least partially, to be freely arranged in the position of the renal arteries, and a lower portion freely moving in a position within the aneurysm and above the iliac arteries, wherein said main body comprises a flexible fabric made of woven material having a very loose weave in the upper portion and a tight weave in the lower portion of the main body, wherein the method comprises the steps of:

a) intraluminally inserting a guide to the affected area of the aorta through the aneurysm and over the renal arteries, b) inserting above the guide a positioning device having a first catheter provided with said prosthesis, which is an expandable balloon prosthesis, so that the anchoring means of the aortic prosthesis is positioned above the renal arteries and the area of the aorta affected by the aneurysm, c) releasing the aortic prosthesis from the tubular positioning device by sliding it out and leaving the aortic prosthesis in its position, d) inflating the expandable balloon to expand the anchoring means against the walls of the aorta so that the anchoring means of the aortic prosthesis is fixedly held above the area of the aorta affected by the aneurysm while the very loose weave is adjacent to the ostia of the renal arteries and the tight weave of the prosthesis is freely positioned within the area of the aneurysm below the renal arteries, e) deflating the expandable balloon, f) removing the first catheter, g) carrying via the guide a second balloon catheter, provided at its distal end with a tip and expandable balloon, to the area of the very loose weave of the aortic prosthesis to be perforated, adjacent to the ostium of a first renal artery, h) piercing or puncturing the very loose weave by means of the tip of the distal end of the second balloon catheter to generate an opening for passage of said distal end, i) passing the distal end of the second balloon catheter through the aperture generated into the interior of the first renal artery, J) positioning the expandable balloon of the second catheter in said opening, k) Inflating the expandable balloon so as to generate a window allowing free passage of blood into the renal arteries and additionally the passage of a catheter or introducer, l) deflating the expandable balloon, m) withdrawing the second balloon catheter, n) carrying via the guide a third catheter provided with a second expandable balloon prosthesis until the second expandable balloon prosthesis is positioned within the window generated in the very loose weave adjacent to the ostium of the first renal artery, o) Inflating the expandable balloon to expand the second prosthesis against the walls of the first renal artery and window of the very loose weave so that the second prosthesis is implanted and fixedly held against the inner walls of the first renal artery and the window generated in the very loose weave, p) deflating the expandable balloon, q) removing the third catheter, r) repeating steps (g) to (q) for the renal artery opposite the first one.

It is further an object of the present invention to provide the method of the previous paragraph wherein the prosthesis further comprises an intermediate portion between said upper and lower portions and said intermediate portion comprises said flexible fabric made of woven material with an intermediate weave fabric, being between very loose and tight, with said intermediate portion being intended to be arranged below the renal arteries.

It is a further object of the invention to provide an aortic prosthesis for the treatment of abdominal aortic aneurysms, wherein the prosthesis comprises a tubular hollow structure intended to be inserted intraluminally into the aorta and secured so as to isolate the aneurysm, maintaining the blood circulation through the aorta and arteries that access the aorta, wherein the prosthesis comprises:

a main body having a generally cylindrical shape with an upper portion intended at least partially to be secured firmly above the aneurysm through an anchoring means and a lower portion intended to be freely arranged at a position within the aneurysm and above the iliac arteries, wherein said upper portion comprises a flexible fabric made of woven material with a very loose weave fabric and said lower portion comprises said flexible fabric made of woven material with a tight weave fabric.

BRIEF DESCRIPTION OF THE DRAWINGS

The present invention is illustrated by way of example in the following drawings wherein:

FIG. 1 shows a sectional side elevational view of a monoiliac-type aortic prosthesis according to the prior art, wherein the prosthesis is already deployed within the aorta and fixed in a healthy neck of the aorta;

FIG. 2 shows a sectional side elevational view of a case involving abdominal aneurysm without a neck for fixing the prosthesis, in accordance with one of the problems that are solved by the present invention;

FIG. 7 shows a side elevational view of a monoiliac-type aortic prosthesis according to the present invention, already deployed within the aorta, where the expandable balloon has not been shown in order to avoid confusion between the balloon and the aortic prosthesis, and thus assisting in the understanding of the object of the present invention;

FIG. 8 shows a sectional side elevational view of a bi-iliac type aortic prosthesis according to the present invention, already deployed within the aorta, wherein the expandable balloon has not been shown in order to avoid confusion between the balloon and the aortic prosthesis, and thus assisting in the understanding of the object of the present invention;

DESCRIPTION OF THE PREFERRED EMBODIMENTS

Figure 3:
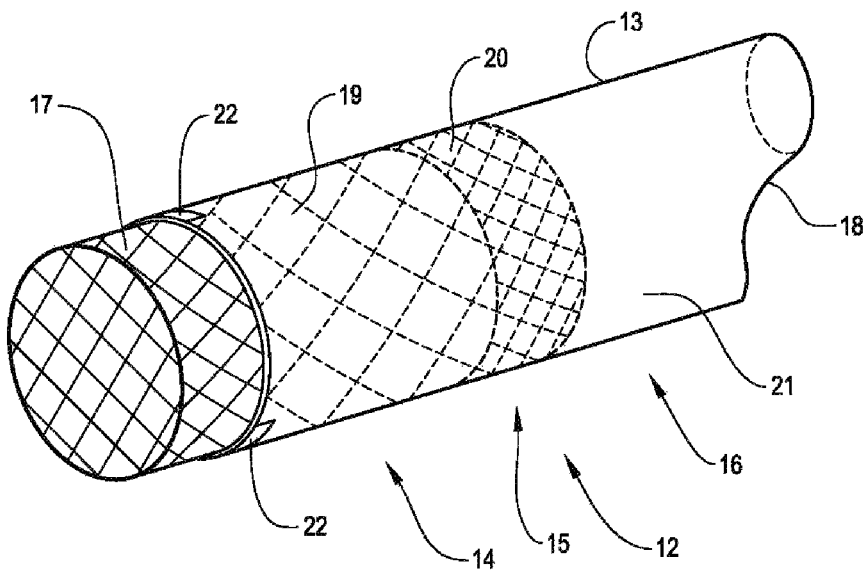
FIG. 3 shows a perspective view of a monoiliac type aortia prosthesis according to the present invention.

Referring now in detail to figures, it is seen that the invention consists of a new aortic prosthesis for the treatment of abdominal aneurysms, which may be deployed intraluminally within the aorta even if the aneurysm does not have an upper proximal aortic neck for anchoring the upper end of the aortic prosthesis.

According to FIG. 1, referring to the prior art and according to one of the embodiments of the U.S. Pat. No. 6,162,246 of the same owner as the present application, an infrarenal aorta generally indicated with the reference number 1 can be seen, which is affected by an aneurysm consisting of an abnormal dilatation of the aortic wall. The aorta exits upwards from the heart (not shown) and runs downwardly until it is divided into the iliac arteries 3 and 4. When the aorta is affected by the aneurysm, an upper proximal aortic neck 5 and a lower distal aortic neck 6 are defined in the upper and lower parts of the aneurysm. It may be that the distal neck 6 is not formed because the wall is also dilated when the aneurysm extends to the bifurcation and also through the iliac arteries. If this condition is not treated, the dilated wall, or aneurysm 2, can rupture, resulting in fatal hemorrhage in a very short time.

At present, a technique is used to access the aorta intraluminally to insert and deploy a graft or prosthesis within the aorta to exclude the aorta from the blood circulatory system. When the prosthesis is deployed in the aorta the prosthesis can be firmly attached to those portions of the aortic wall in good condition to provide a secure fixation, i.e. a secured anchorage and a sealed coupling between the aortic prosthesis and the aorta.

Among the various aortic prostheses, three types of main prostheses may be identified, namely a monoilliac aortic prosthesis comprising a one-piece or two-piece cylindrical prosthesis, a bi-iliac aortic prosthesis consisting of a bifurcated prosthesis comprising a tubular prosthesis with a shape of a "Y", and an aorto-aortic prosthesis (not shown) consisting of a sheath or sleeve with an upper stent or fixing means which is attached to an upper neck of the aorta and a lower stent or fixing means which is attached to a lower aortic neck, when it exists. Aorto-aortic prostheses may not always be used because it is common for the aneurysm to have reached a degree of length wherein the lower aortic neck 6, excessively dilated, has disappeared and the lower end of the prosthesis does not find a firm aortic wall to be fixed to. With respect to bifurcated prostheses, they are designed to have the trunk of the Y inserted and firmly attached to the proximal neck 5 of the aorta while each branch or extension or leg of the Y is inserted and installed within a respective iliac artery 3 and 4.

According to one of the embodiments of U.S. Pat. No. 6,162,246, there is provided a monoiliac prosthesis 7 having an upper end securely fixed to the upper proximal aortic neck 5 through an anchoring means which may be a stent 8, and a lower end 9 intended to be freely within the aneurysm area and above the iliac arteries 3 and 4. In the case of FIG. 1, the aneurysm causes abnormal dilatation 2 of the aortic wall, thus defining the upper 5 and lower 6 aortic necks. However, the upper proximal aortic neck 5 may not be well defined or may disappear because the aneurysm affects that portion generating a complete dilation below the renal arteries 10 and 11, as best shown in FIG. 2. In such a situation, abnormal dilation 2 prevents the formation of an upper aortic neck 5 and consequently prevents anchoring of the upper end of the conventional aortic prosthesis, therefore, if this condition is not treated, the dilated wall or aneurysm 2, can rupture resulting in a fatal hemorrhage in a very short time. It is understood that both the structural configuration and the various embodiments of the conventional prosthesis are sufficiently described in detail in U.S. Pat. No. 6,162,246, the reference of which is attached hereto, and that for such reasons, we will not go into descriptive details about it.

In view of the above, conventional prostheses can not be used when the aneurysm generates an abnormal dilation such that it prevents the formation of an upper proximal aortic neck 5, since there is no secure zone for anchoring the conventional prosthesis. Accordingly, the inventor of the present invention has developed a new prosthesis, either a monoiliac or bi-iliac prosthesis which can be deployed without being affected by the problems and difficulties noted above and to which reference will be made hereinafter.

Thus, and in accordance with FIGS. 3 to 14, and more particularly with FIG. 3, the aortic prosthesis of the present invention is indicated by the general reference 12 and comprises a main body 13 having a generally cylindrical shape with an upper portion 14, an intermediate portion 15 and a lower portion 16. According to FIGS. 7 and 8, the upper portion 14 is partially intended to be securely fixed above the renal arteries 10 and 11 through anchoring means 17 and partially to be freely arranged in the adjacent or opposite position with respect to the ostia of the renal arteries 10 and 11. The intermediate portion 15 is arranged between the renal arteries 10 and 11 and the upper proximal aortic neck 5 affected by the aneurysm 2. While the lower portion 16 moves freely at a position within the aneurysm 2 and above the iliac arteries 3 and 4, said lower portion 16 having a lower edge 18 that can be connected to a leg portion (not shown) sufficiently defined and described in Patent Document U.S. Pat. No. 6,162,244, reference of which is attached herein.

Likewise, the main body 13 comprises a novel flexible fabric made of woven material having a very loose weave fabric 19 in the upper portion 14, an intermediate weave fabric 20 between very loose and tight, in the intermediate portion 15, and a tight weave fabric 21 in the lower portion 16. This body is woven with multifilament polyester yarn, textured in machines that allow the change of the weave density so that it allows the variation in different sections of the amount of columns and passes by centimeter. This variation gives the 3 portions different physical and biological properties. In an exemplary embodiment, but not limited to the invention, the following properties may be available:

A—Physical properties:

1—Density of the mesh (columns/cm×passes/cm):

The very loose fabric of the very loose weave 19 in the upper portion 14 has a weave density of 12 columns/centimeter by 9 passes/cm. The intermediate weave 20 in the intermediate portion 15 has a weave density of 14 columns/centimeter by 12 passes/cm. The tight weave 21 in the lower portion 16 has a weave density of 16 columns/centimeter by 20 passes/cm.

2—Longitudinal tensile strength:

Fabric of a very loose weave 19: 52 kg; fabric of an intermediate weave 20 intermediate: 89 kg; y fabric of a tight weave 21: 103 kg.

3—Transverse tensile strength:

Fabric of a very loose weave 19: 23 kg/cm; fabric of an intermediate weave 20: 52 kg/cm; y fabric of a tight weave 21: 79 kg/cm.

4—Perzos bursting strength:

Fabric of a very loose weave 19: 7 kg; fabric of an intermediate weave 20: 20 kg; y fabric of a tight weave 21: 35 kg.

5—Breaking strength of fibers of the fabric of a very loose weave 19 faced to the use of a balloon of 6 mm in diameter: 12 atmospheres.

B—Biological properties:

1—The density of weaves of the intermediate weave 20 and tight weave 21 produce the vascular occlusion when they plug side arteries and renal arteries.

2—The density of the fabric of a very loose weave allows a constant flow towards the renal arteries during the implant of the prosthesis.

3—The fibrin deposit on the wall of meshes of intermediate and tight weave fabric immediately seals the pores of the prosthesis tube even before reversing the effects of heparin when finishing the implant.

4—The lowest weave density of the very loose weave fabric hinders, slows or prevents the sealing of the pores through the fibrin deposit.

As mentioned above, these properties are exemplary but do not limit the present invention. It is emphasized that the weave may be a knitted weave, or a jersey weave. On its turn, in order to carry out the embodiment of the different sections of the weave provided in the prosthesis of the present invention, double face or circular rectilinear knitting machines can be used which allow to modify the number of passes per linear centimeter of the fabric, making the weave more lax or tighter as required, not being limiting to the invention.

When the aortic prosthesis of the invention is implanted in the aorta, the very loose weave 19 ensures passage of blood flow to the renal arteries 10 and 11. The intermediate tissue 20 is, in turn, arranged so as to avoid a sharp cut of the weave between the very loose and tight part, providing greater flexibility. Likewise, the arrangement of the intermediate tissue 20 allows the passage of blood fluid into the renal arteries in cases where the prosthesis is implanted such that a part of the intermediate tissue is adjacent to or in front of the ostia of the renal arteries. The tight weave 21, for its part, is arranged within the aneurysm and below the renal arteries 10 and 11. It is emphasized that the very loose weave portion of the prosthesis of the invention may extend to the upper mesenteric artery and the celiac trunk, which are located above the renal arteries.

Figure 4:
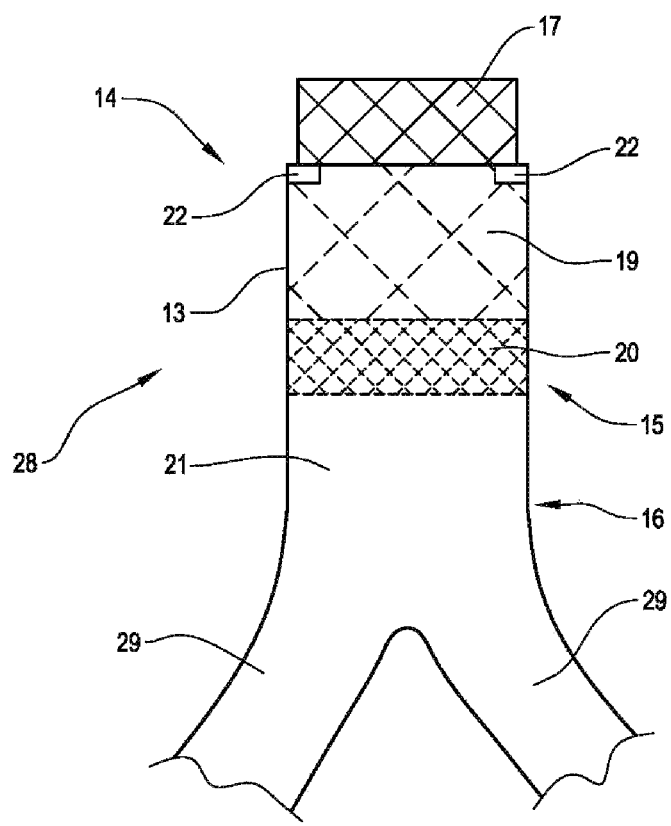
FIG. 4 shows a side view of a bi-iliac-type prosthesis according to the present invention.
Figure 6:
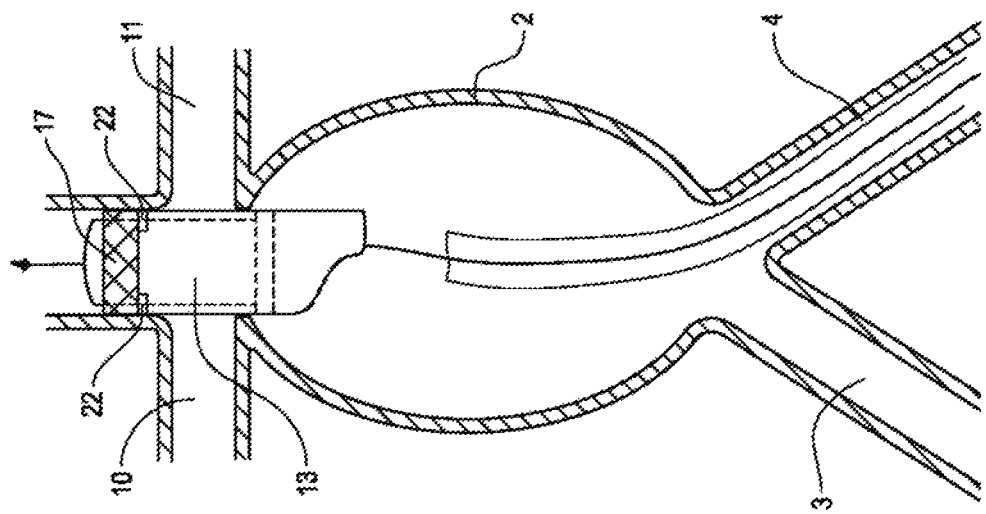
FIG. 6 shows a sectional side elevational view of a step following the step of FIG. 5, wherein an expandable balloon is inflated and expanded to implant to the aortic prosthesis of the invention, wherein, in addition, the prosthesis has been illustrated for exemplary purposes and for such reasons it is disproportionated to the anchoring means.
Figure 5:
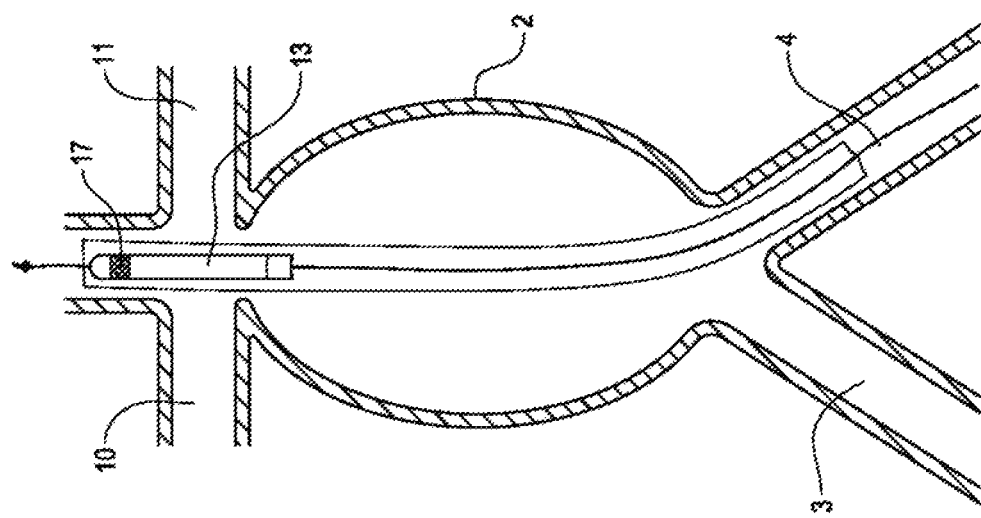
FIG. 5 shows a sectional side elevational view of a step for implanting the prosthesis according to the present invention, wherein one can see the aortic prosthesis positioned in the implant zone, more precisely in the area of the renal arteries because there is no healthy aortic neck where to fix the prosthesis.

Referring again to the anchoring means 17, it comprises a plastically deformable material defined by a stent having a portion fixed to the very loose weave 19 of the main body, extending to the beginning of the most tight weave, i.e. it may extend from the very loose weave towards at least part or all of the intermediate weave which will allow it to expand, and part of the tight weave. Likewise, the stent has a portion protruding beyond the very loose weave 19 and which is securely fixed to said aortic portion above the renal arteries 10 and 11. In this way, the anchoring means 17 is fixed within the aorta portion above renal arteries and partly below the renal arteries, and is securely fixed to the portion by means of a radially expandable balloon which is removably arranged by means of a catheter, so that the anchoring means is implanted by expansion against the aorta portion above and partially at a point below the renal arteries 10 and 11. It is clarified that FIGS. 3 and 4 show that the stent 17 extends to the portion where the tight weave 21 begins, this not limiting the invention, since the stent 17 may be partially extended both within the intermediate weave and the tight weave. At the same time, it is pointed out that, in order to facilitate the placement of the prosthesis within the aorta, radiopaque markers 22 are provided in the portion of the loosest weave fabric, i.e. the marks indicate the extent of the loose weave to be positioned at the level of the renal arteries.

In this way, the prosthesis of the present invention is positioned within the aorta by means of a tubular positioning device such as an introducer or sheath. It is emphasized that, prior to the introduction of the tubular positioning device, a guide should be introduced intraluminally that will be positioned within the aorta. In turn, the tubular positioning device has a first catheter provided with an expandable balloon prosthesis, which for the case of the invention, the prosthesis corresponds to the aortic prosthesis. For this purpose, the prosthesis is folded in multiple folds and compressed so as to fit tightly within the tubular positioning device, the tubular positioning device being then introduced into the blood circulatory system of a patient to access the aorta with the prosthesis in the device. Once it is in the desired location where the prosthesis is to be implanted, in the case of the invention with the anchoring means protruding from the main body above the area of the aorta affected by the aneurysm, the prosthesis is released from the tubular positioning device by sliding it out and leaving the prosthesis in position and the expandable balloon is inflated to expand the prosthesis so that the anchoring means of the aortic prosthesis is fixedly held above the area of the aorta affected by the aneurysm, i.e. above the renal arteries 10 and 11, while the very loose weave 19 is positioned in front of or adjacent to the ostia of the renal arteries and the tight weave 21 of the aortic prosthesis is freely positioned within the aneurysm area. Once the prosthesis is implanted, the expandable balloon is deflated and then the first catheter is removed.

In this way, the aortic prosthesis is implanted in such a way that the very loose weave 19 is positioned adjacent to the ostia of the renal arteries. Being a very loose weave, it allows the passage of blood flow to the renal arteries for enough time which avoids risks for the patient. In the case where the prosthesis is implanted and a portion of the intermediate weave 20 is positioned adjacent to the ostia of the renal arteries, this will not generate a complication in the patient, because the intermediate weave also allows the passage of blood fluid, but for less time, as mentioned above.

The aortic prosthesis of the invention is provided with the anchoring means 17, preferably a stent, generally consisting of an expandable metal mesh capable of being expanded and maintaining its expanded configuration after the balloon, which has expanded it, is deflated. Each stent or foxing means is located on an expandable balloon, therefore, once the balloon is expanded the stent is deformed radially outwardly so that it is firmly secured against the wall of the aorta, in a healthy portion thereof, covering the renal arteries with the portion of looser weave. FIGS. 7 and 8 show the stent 17 which is attached to a portion of the aorta and above the renal arteries 10 and 11.

It is noted that the stent 17 may alternatively be made of a resilient type with a tendency to expand towards its relaxed condition to a maximum fixed diameter when the stent is released from its compressed condition into which it is loaded into the catheter, or, the stent may be of the rigid type in which case the stent is made of a metal mesh which is also loaded in a compressed condition within the catheter but is radially deformed outwardly by the balloon to bring it into a permanent expanded condition. A stent of the rigid type is capable of retaining a permanent expanded deformation to firmly hold the prosthesis against forces arising from the blood flow and movements of the patient. The stent 17 is made of a suitable biomedical grade metal.

Figure 9:
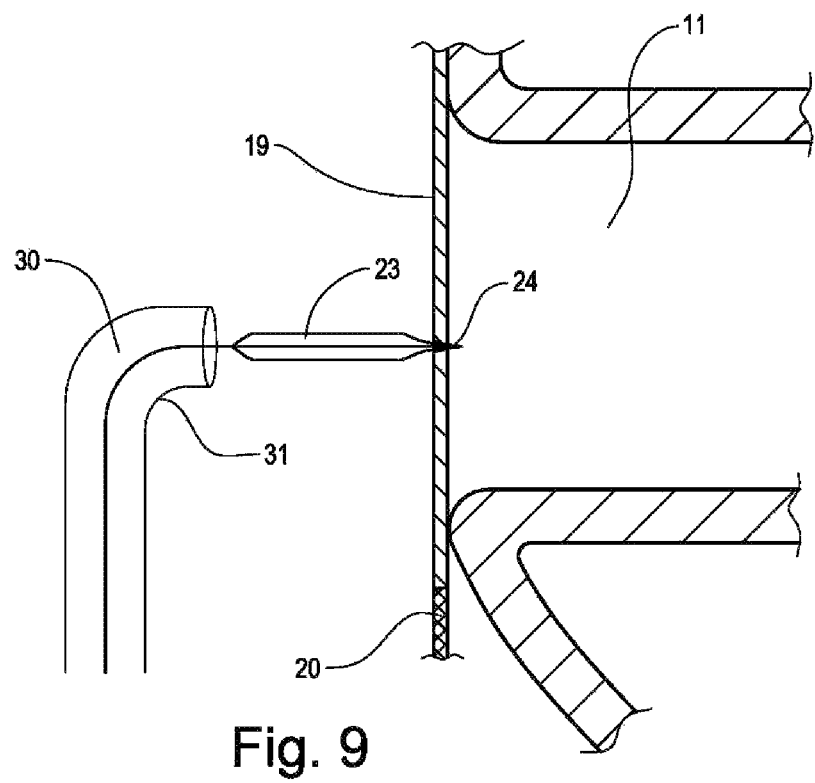
FIG. 9 shows a partial and sectional side elevational view of a step for puncturing one of the walls of the aortic prosthesis according to the present invention, wherein one can see the distal end of a second catheter puncturing or piercing said wall of the prosthesis adjacent to or facing the ostium of one of the renal arteries.
Figure 10:
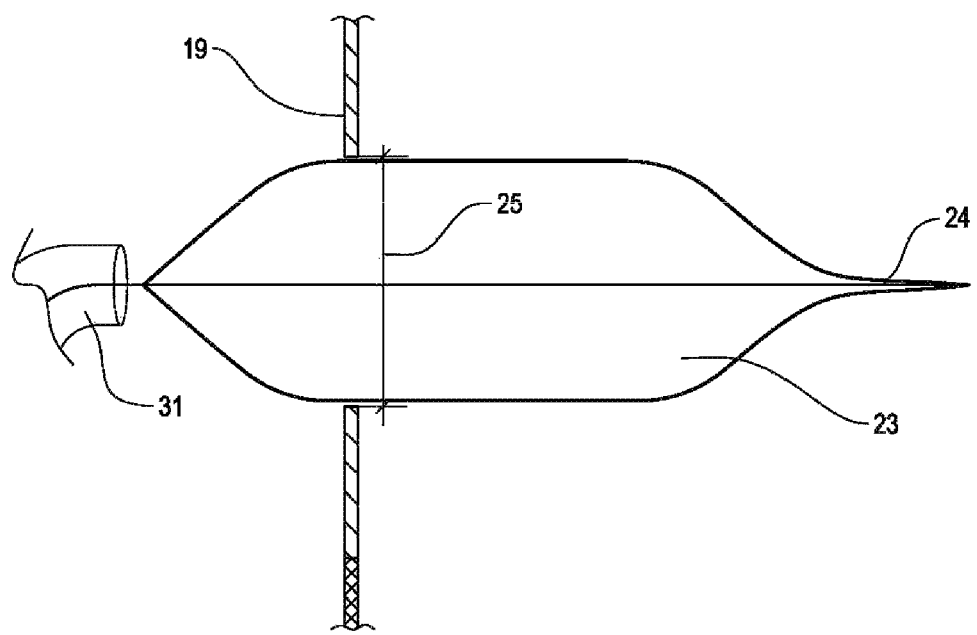
FIG. 10 shows a partially sectional side elevational view of a step following the step of FIG. 9, wherein an expandable balloon is inflated and expanded to open a window in the wall of the prosthesis.

Thus, once the aortic prosthesis of the present invention is implanted, the section of very loose weave 19 is arranged adjacent to the ostia of the renal arteries 10 and 11, as mentioned above. Being a very loose section, the passage of flow is not momentarily obstruct in its entirety, however, to prevent it from being completely closed, one may proceed as follows: a second balloon catheter provided at its distal end with a tip 24 and expandable balloon 23 is carried by the guide and into a sheath 30, preferably with an elbowed end 31, well known in the art, in order to carry out the perforation of the very loose weave portion 19 which is arranged adjacent to the renal artery 11, as best illustrated in FIG. 9. Once in position, the very loose weave 19 is pierced or punctured by the tip of the distal end so as to generate an opening through which the distal end of the second catheter can pass. Once the opening is generated, the tip 23 is passed through the opening and into the renal artery 11, positioning the expandable balloon 23 in said opening. Thereafter, the expandable balloon 23 is inflated so as to provide a window 25 which allows free passage of blood into the renal arteries and, in turn, the passage of a third catheter which will be described below, as best illustrated in FIG. 10 for the installation of a lined stent to which reference will be made later. It is noted that the very loose weave is broken with a balloon of 6 mm in diameter, inflated to more than 12 atmospheres, wherein the mesh of the very loose weave is not torn after the fibers thereof are broken.

Figure 11:
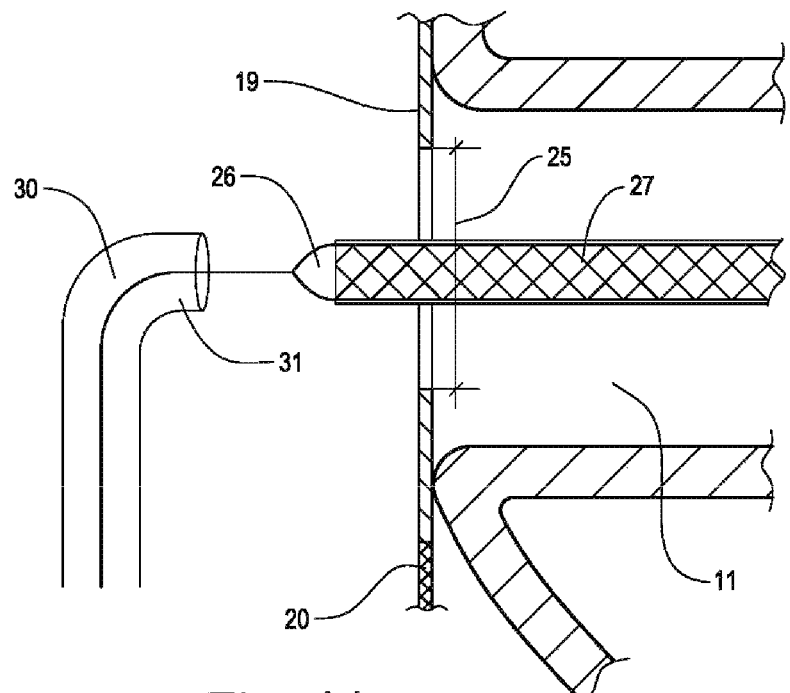
FIG. 11 shows a partially sectional side elevational view of a step following the step of FIG. 10, wherein an expandable balloon prosthesis is positioned within the previously generated window.
Figure 12:
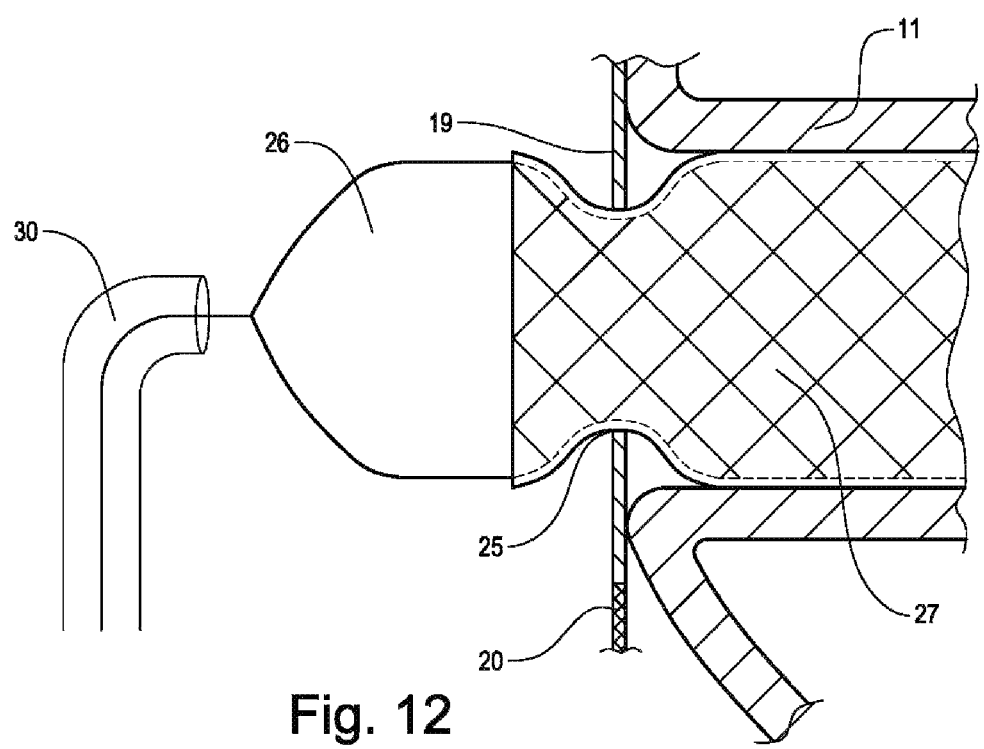
FIG. 12 shows a partially sectional side elevational view of the prosthesis of FIG. 11 already deployed within one of the renal arteries and sealed in the window of the wall of the prosthesis.

After perforating or tearing the very loose weave 19 adjacent to the ostium of the renal artery 11, the expandable balloon 23 is deflated, the second balloon catheter is withdrawn, and a third catheter or introducer (not shown) is introduced with at least one expandable balloon prosthesis 26 provided with a prosthesis or graft 27 which may comprise a lined stent, as best illustrated in FIG. 11. The third catheter is led by the guide towards the renal artery 11 so that the expandable balloon prosthesis is partially positioned within the window 25 generated in the very loose weave 19 and within the renal artery 11. Once in position, FIG. 12, the expandable balloon 26 is inflated to expand the prosthesis 27 against the walls of the first renal artery and window 25 of the very loose weave, so that the prosthesis 27 is implanted and fixedly held against the inner walls of the first renal artery and sealed against the window generated in the very loose weave. Once the prosthesis 27 is implanted, the expandable balloon is deflated and the third catheter is removed.

It is noted that the steps for perforating the very loose weave and the subsequent implantation of the prosthesis 27 should be repeated for the renal artery 10. In turn, it is recalled that according to the use of the invention, the guide wire 24 is inserted first into the blood circulatory system and is moved until it reaches the aorta by making an incision in a blood vessel at a remote site of the aorta. Preferably, the incision is made in the patients groin to enter through the femoral artery; however, this incision can be made in any other blood vessel as far as the aorta can be safely accessed. Also, as an aid in the correct positioning of the prosthesis, there are provided the radiopaque markers or indicators 22 as is well known in the art.

Figure 14:
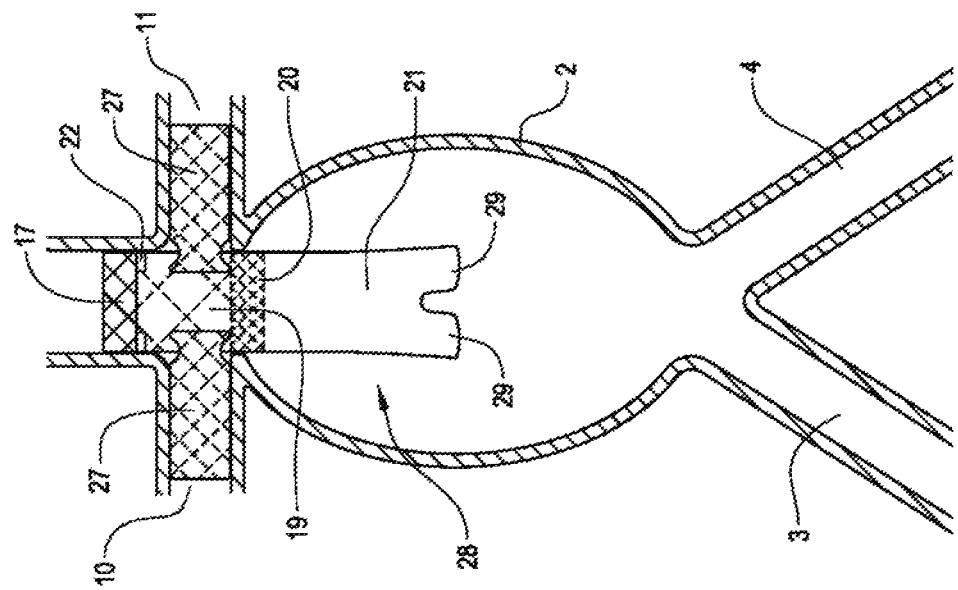
FIG. 14 shows a partially sectional side elevational view, of the aortic prosthesis of the present invention, of the bi-iliac type, already deployed within the aorta and together with any prostheses already deployed in the renal arteries.
Figure 13:
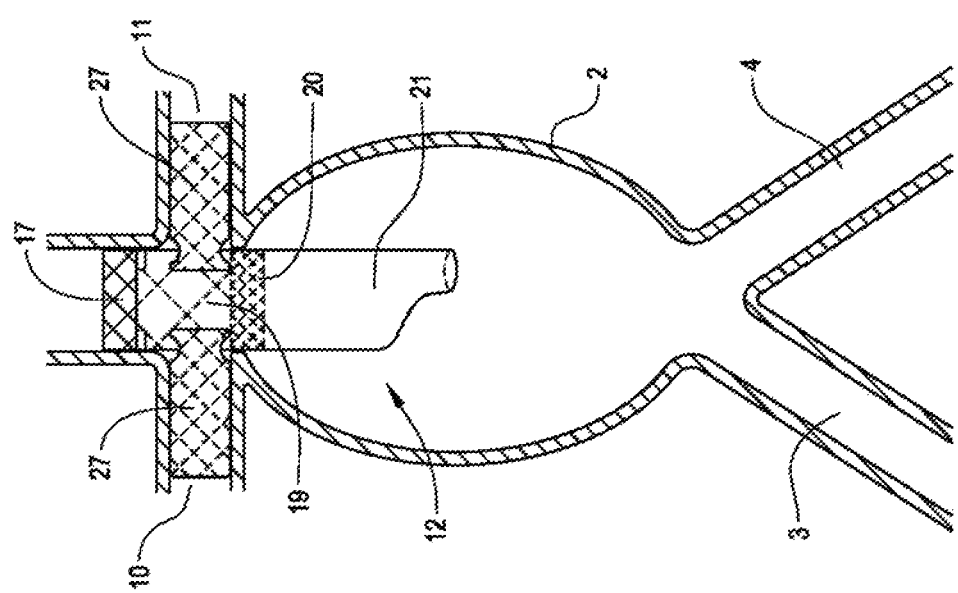
FIG. 13 shows a partially sectional side elevational view of the aortic prosthesis of the present invention, of the mono-iliac type, already deployed within the aorta and together with any prostheses already deployed in the renal arteries.

Thus, as seen in FIGS. 13 and 14, the renal arteries are in fluid communication with the prosthesis of the present invention, allowing the passage of blood flow without any inconvenience and further, by successfully isolating the abdominal aneurysm. To complete the treatment of the abdominal aneurysm, the prosthesis of the present invention may be connected to a leg such as that described in U.S. Pat. No. 6,162,246 and which is implanted between one or both iliac arteries, depending on whether the prosthesis is mono- or bi-iliac, and the lower edge or end of the prosthesis of the invention. Both the structural configuration, advantages and method of installation of the leg are sufficiently described and illustrated in the patent document U.S. Pat. No. 6,162, 246 of the same owner as the present patent application and for such reasons, we will not go into descriptive details about them.

Alternatively, FIGS. 4, 8 and 14, the lower portion of the aortic prosthesis of the present invention may comprise a bi-iliac prosthesis 28 having a prosthesis main portion with a generally cylindrical and bifurcated shape, which resembles a pair of trousers with two hanging legs 29. The connection between the bi-iliac prosthesis and legs is also sufficiently described in Patent Document U.S. Pat. No. 6,162,246.

It is emphasized that the connection between the lower portion of the aortic prosthesis of the present invention and the legs is not part of the inventive object of the present application and therefore they do not interfere with the object and scope of the invention. That is, the invention focuses on the treatment of abdominal aneurysm when said aneurysm is dilated such that there is no upper proximal aortic neck portion below the renal arteries on which conventional prostheses can be anchored. Thus, with the prosthesis and the use of the present invention, the problems and drawbacks of conventional prostheses and the methods and uses of implantation thereof are avoided or at least minimized when the abdominal aneurysm affects the portion of the upper proximal aortic neck 5. Thus, aneurysm 2, which also affects the aortic wall in the area of the upper proximal aortic neck, can be successfully isolated because the prosthesis of the invention is anchored higher than the renal arteries where internal walls of the aorta allow a proper and correct fixation and sealing, leaving in turn, a continuous passage without obstructions between the renal arteries and the prosthesis.

While preferred embodiments of the present invention have been described and illustrated, it will be apparent to those skilled in the art that various changes and modifications may be made without departing from the scope of the invention as defined in the appended claims.

The invention claimed is:

1. An aortic prosthesis for the treatment of abdominal aortic aneurysms, wherein the prosthesis comprises a tubular hollow structure intended to be inserted intraluminally into the aorta, and fixed so as to isolate the aneurysm, maintaining blood flow through the aorta and through arteries accessing to the aorta, wherein the prosthesis comprises:
   a main body comprising a single flexible fabric made of a knitted material and having a generally cylindrical shape with an upper portion intended at least partially to be secured firmly above the aneurysm through an anchoring means,
   a lower portion intended to be freely arranged at a position within the aneurysm and above the iliac arteries and an intermediate portion, between said upper and lower portions,
   wherein said upper portion, said intermediate portion and said lower portion are formed by said single flexible fabric made of knitted material, with the flexible fabric, in the upper portion, having a weave density of 12 columns/centimeter by 9 passes/cm, in the intermediate portion, a weave density of 14 columns/centimeter by 12 passes/cm and, in said lower portion, a weave density of 16 columns/centimeter by 20 passes/cm.

2. The prosthesis of claim 1, wherein the anchoring means is secured within the aortic portion above the renal arteries and is securely fixed to said aortic portion by means of a radially expandable balloon which is arranged removably by means of a catheter, so that anchoring means is implanted by expansion against the aortic portion above the renal arteries.

3. The prosthesis of claim 1, wherein said anchoring means is self-expanding and elastic and has a portion extending from the upper portion to at least part or all of the intermediate weave and part of the lower portion and a portion protruding beyond the upper portion and being securely fixed to said portion of the aorta above the renal arteries.

4. The prosthesis of claim 1, wherein radiopaque markers are provided along the portion of the fabric in the upper portion.

5. The prosthesis of claim 1, wherein the upper portion has a longitudinal tensile strength of at least 52 kg.

6. The prosthesis of claim 1, wherein the upper portion has a transverse tensile strength of at least 23 kg/cm.

7. The prosthesis of claim 1, wherein the upper portion has a Perzos bursting strength lower than 7 kg.

8. The prosthesis of claim 1, wherein the intermediate portion has a longitudinal tensile strength of at least 89 kg.

9. The prosthesis of claim 1, wherein the intermediate portion has a transverse tensile strength of at least 52 kg/cm.

10. The prosthesis of claim 1, wherein the intermediate portion has a Perzos bursting strength of at least 20 kg.

11. The prosthesis of claim 1, wherein said flexible fabric is a jersey weave.

12. The prosthesis of claim 1, wherein the prosthesis is a bi-iliac prosthesis having a main prosthesis portion having a generally cylindrical and bifurcated shape resembling a pair of trousers with two hanging legs.

13. A method for implanting the prosthesis of claim 1, wherein the method comprises the steps of:
   a) intraluminally inserting a guide to the affected area of the aorta through the aneurysm and over the renal arteries,
   b) inserting above the guide a positioning device having a first catheter provided with said prosthesis, which is an expandable balloon prosthesis, so that the anchoring means of the aortic prosthesis is positioned above the renal arteries and the area of the aorta affected by the aneurysm,
   c) releasing the aortic prosthesis from the tubular positioning device by sliding it out and leaving the aortic prosthesis in its position,
   d) Inflating the expandable balloon to expand the anchoring means against the walls of the aorta so that the anchoring means of the aortic prosthesis is fixedly held above the area of the aorta affected by the aneurysm while the upper portion is adjacent to the ostia of the renal arteries and the lower portion of the prosthesis is freely positioned within the area of the aneurysm below the renal arteries,
   e) deflating the expandable balloon,
   f) removing the first catheter,
   g) carrying via the guide a second balloon catheter, provided at its distal end with a tip and expandable balloon, to the area of the upper portion of the aortic prosthesis to be perforated, adjacent to the ostium of a first renal artery,
   h) piercing or puncturing the upper portion by means of the tip of the distal end of the second balloon catheter to generate an opening for passage of said distal end,
   i) passing the distal end of the second balloon catheter through the aperture generated into the interior of the first renal artery,
   J) positioning the expandable balloon of the second catheter in said opening,
   k) Inflating the expandable balloon so as to generate a window allowing free passage of blood into the renal arteries and additionally the passage of a catheter or introducer,
   l) deflating the expandable balloon,
   m) withdrawing the second balloon catheter,
   n) carrying via the guide a third catheter provided with a second expandable balloon prosthesis until the second expandable balloon prosthesis is positioned within the window generated in the upper portion adjacent to the ostium of the first renal artery,
   o) Inflating the expandable balloon to expand the second prosthesis against the walls of the first renal artery and window of the upper portion so that the second prosthesis is implanted and fixedly held against the inner walls of the first renal artery and the window generated in the upper portion,
   p) deflating the expandable balloon,
   q) removing the third catheter,
   r) repeating steps (g) to (q) for the renal artery opposite the first one.

14. The method of claim 13, wherein the fibers of the upper portion are broken with an expandable balloon of 6 mm in diameter, inflated at more than 12 atmospheres.

15. The method of claim 14, wherein the fabric, in the upper portion, does not tear after its fibers are broken.

16. The method of claim 14, further comprising an intermediate portion between said upper and lower portions and said intermediate portion comprises said flexible fabric of knitted material, wherein the intermediate portion has a weave density of 14 columns/centimeter by 12 passes/cm and it is intended to be arranged below the renal arteries.

\* \* \* \* \*